United States Patent [19]

Zoller et al.

[11] Patent Number: 5,397,796

[45] Date of Patent: Mar. 14, 1995

[54] 2,4-DIOXOIMIDAZOLIDINE COMPOUNDS AND COMPOSITIONS, AND PROCESSES FOR ADMINISTERING SAME

[75] Inventors: Gerhard Zoller, Schöneck; Wolfgang König, Hofheim; Jochen Knolle, Kriftel; Melitta Just, Langen; Bernd Jablonka, Bad Soden, all of Germany

[73] Assignee: Cassella AG, Frankfurt am Main, Germany

[21] Appl. No.: 45,994

[22] Filed: Apr. 12, 1993

[30] Foreign Application Priority Data

Apr. 24, 1992 [DE] Germany ............... 42 13 634.2

[51] Int. Cl.$^6$ ............... A61K 37/02; C07D 233/72; C07D 233/76
[52] U.S. Cl. ............... 514/389; 514/391; 514/385; 514/398; 548/319.5
[58] Field of Search ............... 548/319.5, 399, 385, 548/389, 391

[56] References Cited

U.S. PATENT DOCUMENTS

| | | | |
|---|---|---|---|
| 3,300,510 | 1/1967 | Alburn et al. | 548/319.5 X |
| 4,237,131 | 12/1980 | Wootton et al. | 424/248.51 |
| 5,100,907 | 3/1992 | Hall et al. | 514/385 |

FOREIGN PATENT DOCUMENTS

| | | | |
|---|---|---|---|
| 7365391 | 10/1991 | Australia | 548/319.5 |
| 0449079 | 10/1991 | European Pat. Off. | 548/319.5 |
| 2714655 | 10/1978 | Germany | 548/319.5 |

OTHER PUBLICATIONS

Jornal of the Chem. Society, Dec. 1965, London, GB, pp. 6806–6813.

*Primary Examiner*—Floyd D. Higel
*Attorney, Agent, or Firm*—Perman & Green

[57] ABSTRACT

The present invention relates to 2,4-dioxoimidazolidine compounds of the formula I

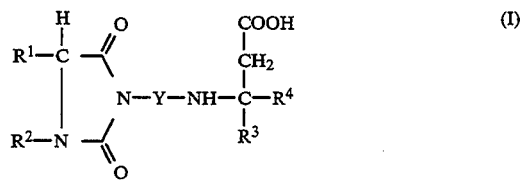

a process for their preparation and their use as inhibitors of platelet aggregation, metastasis of carcinoma cells and osteoclast binding to the bone surfaces.

5 Claims, No Drawings

2,4-DIOXOIMIDAZOLIDINE COMPOUNDS AND COMPOSITIONS, AND PROCESSES FOR ADMINISTERING SAME

BACKGROUND OF THE INVENTION

1. Field of the Invention

The present invention relates to 2,4-dioxoimidazolidine derivatives, their preparation and their use as inhibitors of blood platelet aggregation.

2. Discussion of the Prior Art

Hydantoin derivatives having thrombocyte aggregation-inhibiting action are described in EP-A 449,079, and in the unpublished German Patent Application P 41 26 277.8. Further research has shown that the compounds of the present invention are also potent inhibitors of blood platelet aggregation.

SUMMARY OF THE INVENTION

The present invention relates to compounds of the general formula I $$\begin{array}{c} \text{H} \quad \text{O} \quad\quad \text{COOH} \\ | \quad \| \quad\quad | \\ R^1-C-\diagup \quad\quad CH_2 \\ \quad\quad\quad | \\ \quad N-Y-NH-C-R^4 \\ R^2-N-\diagdown \quad\quad | \\ \quad\quad \| \quad\quad R^3 \\ \quad\quad O \end{array} \quad (I)$$

in which

Y denotes $-(CH_2)_m-CO-$, where m represents an integer from 1 to 4, or $$\text{(phenyl)}-CO-;$$

$R^1$ denotes $-(CH_2)_n-NH-X$, where n represents an integer from 1 to 6, $-(CH_2)_p-C_6H_4-NH-X$, $-(CH_2)_p-C_6H_4-C(=NH)-NH_2$ or $-(CH_2)_p-C_6H_4-CH_2-NH-X$, where p in each case represents 1 or 2, but also where instead of $$\diagdown CH-R^1 \quad \diagdown C=CH-C_6H_4-X^1 \text{ can be present}$$

$X^1$ denotes $-NHX$, $-CH_2NHX$ or $-C(=NH)-NH_2$;

X denotes hydrogen, $(C_1-C_6)$-alkyl or a radical of the formula II $$R'-NH-C=N-R'' \quad (II)$$

where R' and R" independently of one another represent hydrogen or $(C_1-C_6)$-alky;

$R^2$ denotes hydrogen or $(C_1-C_6)$-alkyl;

$R^3$ denotes hydrogen or phenyl;

$R^4$ denotes $-COOR^5$, $CO-N(CH_3)-R^5$ or $-CO-NH-R^5$;

$R^5$ denotes $(C_1-C_{26})$-alkyl which is substituted a) by mono- or di-$(C_1-C_{18})$-alkylaminocarbonyl, amino-$(C_2-C_{14})$-alkylaminocarbonyl, amino-$(C_1-C_3)$-alkylphenyl-$(C_1-C_3)$-alkylaminocarbonyl, $(C_1-C_{18})$-alkylcabonylamino-$(C_1-C_3)$-alkylphenyl-$(C_1-C_3)$-alkylaminocarbonyl or $(C_1-C_{18})$-alkylcarbonylamino-$(C_2-C_{14})$-alkylaminocarbonyl, where the alkyl radicals for their part can be substituted by hydroxyl, amino, mercapto, $(C_1-C_{18})$-alkoxy, halogen, nitro, trifluoromethyl, $(C_6-C_{14})$-aryl or $(C_6-C_{14})$-aryl-$(C_1-C_8)$-alkyl and which b) is optionally additionally monosubstituted or polysubstituted by identical or different radicals from the series consisting of hydroxyl, hydroxycarbonyl, aminocarbonyl, amino, mercapto, $(C_1-C_{18})$-alkoxy, $(C_1-C_{18})$-alkoxycarbonyl, $(C_6-C_{14})$-aryl-$(C_1-C_3)$-alkoxycarbonyl, $(C_3-C_8)$-cycloalkyl, halogen, nitro, trifluoromethyl and a radical $R^6$;

$R^6$ denotes $(C_6-C_{14})$-aryl, $(C_6-C_{14})$-aryl-$(C_1-C_8)$-alkyl, a monocyclic or bicyclic 5- to 12-membered heterocyclic ring which can be aromatic, partially hydrogenated or completely hydrogenated and which, as the heteroelement, can contain one, two or three identical or different nitrogen, oxygen or sulphur atoms, or denotes a radical $R^7$, where the arly radical and, independently thereof, the heterocyclic radical can be optionally monosubstituted or polysubstituted by identical or different radicals from the series consisting of $(C_1-C_{18})$-alkyl, $(C_1-C_{18})$-alkoxy, halogen, nitro and trifluoromethyl;

$R^7$ denotes $-NR^8R^9$, $-OR^8$, $-SR^8$, an amino acid side chain, a natural or unnatural amino acid residue, imino acid residue, optionally N-$(C_1-C_8)$-alkylated or $(C_6-C_{14})$-aryl-$(C_1-C_8)$-alkylated azaamino acid residue or dipeptide residue, in which the peptide bond can be reduced to $NH-CH_2$, and also their esters and amides, where free functional groups can optionally be substituted by hydrogen or hydroxymethyl or be protected by protective groups customary in peptide chemistry, or denotes a radical $-COR^{7'}$, in which $R^{7'}$ is defined as $R^7$;

$R^8$ denotes hydrogen, $(C_2-C_{18})$-alkyl, $(C_6-C_{14})$-aryl-$(C_1-C_8)$-alkyl, $(C_1-C_{18})$-alkylcarbonyl, $(C_1-C_{18})$-alkoxycarbonyl, $(C_6-C_{14})$-arylcarbonyl, $(C_6-C_{14})$-aryl-$(C_1-C_8)$-alkylcarbonyl, or $(C_6-C_{14})$-aryl-$(C_1-C_{18})$-alkoxycarbonyl, where the alkyl groups can optionally be substituted by an amino group, a natural or unnatural amino acid residue, imino acid residue, optionally N-$(C_1-C_8)$-alkylated or $(C_6-C_{14})$-aryl-$(C_1-C_8)$-alkylated azaamino acid residue or a dipeptide residue, in which the peptide bond can be reduced to $NH-CH_2$; and $R^9$ denotes hydrogen, $(C_1-C_{18})$-alkyl, $(C_6-C_{14})$-aryl or $(C_6-C_{14})$-aryl-$(C_1-C_8)$-alkyl; and their physiologically tolerable salts.

Alkyl radicals can be straight-chain or branched. Preferred alkyl radicals are methyl, ethyl, n-propyl, i-propyl, n-butyl, i-butyl, sec-butyl and tert-butyl. The same applies to radicals such as alkoxy, alkoxycarbonyl or aralkyl.

$(C_3-C_8)$-Cycloalkyl radicals are in particular cyclopropyl, cyclobutyl, cyclopentyl, cyclohexyl, cycloheptyl and cyclooctyl, which, however, can also be substituted by, for example, $(C_1-C_4)$-alkyl. Examples of substituted cycloalkyl radicals are 4-methylcyclohexyl and 2,3-dimethylcyclopentyl.

( $C_6-C_{14}$)-Aryl groups are, for example, phenyl, naphthyl, biphenylyl or fluorenyl, phenyl and naphthyl being preferred. The same applies to radicals such as aralkyl or arylcarbonyl. Aralkyl radicals are in particular benzyl and also 1- and 2-naphthylmethyl, which can also be substituted. Substituted aralkyl radicals are, for example, halobenzyl or ($C_1$–$C_4$)-alkoxybenzyl.

If phenyl is disubstituted, the substituents can be present in the 1,2-, 1,3- or 1,4-position to one another. The 1,3- and the 1,4-positions are preferred, Heterocycles within the meaning of the above definitions are, for example, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindazolyl, indazolyl, phthalazinyl, quinolyl, isoquinolyl, quinoxalinyl, quinazolinyl, cinnolinyl or a benzofused, cyclopenta-, cyclohexa- or cyclohepta-fused derivative of these radicals.

These heterocycles can be substituted on a nitrogen atom by oxides, ($C_1$–$C_7$)-alkyl, for example methyl or ethyl, phenyl or phenyl-($C_1$–$C_4$)-alkyl, for example benzyl, and/or on one or more carbon atoms by ($C_1$–$C_4$)-alkyl, halogen, hydroxyl, ($C_1$–$C_4$)-alkoxy, for example methoxy, phenyl-($C_1$–$C_4$)-alkoxy, for example benzyloxy, or oxo and can be partially or completely saturated.

Radicals of this type are, for example, 2- or 3-pyrrolyl, phenylpyrrolyl, for example 4- or 5-phenyl-2-pyrrolyl, 2-furyl, 2-thienyl, 4-imidazolyl, methylimidazolyl, for example 1-methyl-2-, 4- or 5-imidazolyl, 1,3-thiazol-2-yl, 2-, 3- or 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, for example 1-methyl-, 5-methyl-, 5-methoxy, 5-benzyloxy, 5-chlorine or 4,5-dimethyl-2-indolyl, 1-benzyl-2- or 3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxylinyl, 2-benzofuranyl, 2-benzothienyl, 2-benzoxazolyl or benzothiazolyl. Partially hydrogenated or completely hydrogenated heterocyclic rings are, for example, dihydropyridinyl, pyrrolidinyl, for example 2-, 3- or 4-N-methylpyrrolidinyl, piperazinyl, morpholinyl, thiomorpholinyl, tetrahydrothienyl, benzodioxolanyl.

Halogen represents fluorine, chlorine, bromine or iodine, in particular fluorine or chlorine.

Natural and unnatural amino acids can be present, if they are chiral, in the D- or L-form. α-Amino acids are preferred. For example, the following may be mentioned (cf. Houben-Weyl, Methoden der organischen Chemie (Methods of organic chemistry), Volume XV/1 and 2, Stuttgart, 1974):

Aad, Abu δAbu, ABz, 2ABz, Aca, Ach, Acp, Adpd, Ahb, Aib, βAib, Ala, βAla, aAla, Alg, All, Ama, Amt, Ape, Apm, Apr, Arg, Ash, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guy, hAla, hArg, hCys, hGln, hGlu, His, bile, bleu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Set, Thi, βThi, Thr, Thy, Thx, Tia, Tle, Tly, Trp, Trta, Tyr, Val, Tbg, Npg, Chg, Cha, Thia, 2,2-diphenylaminoacetic acid, 2-(p-tolyl)-2-phenylaminoacetic acid and 2-(p-chlorophenyl)aminoacetic acid.

Amino acid side chains are understood as meaning side chains of natural or unnatural amino acids. Azaamino acids are natural or unnatural amino acids, the central component —CHR— or —CH$_2$— being replaced by —NR— or —NH— respectively.

Suitable radicals of an imino acid are in particular radicals of heterocycles from the following group:

Pyrrolidine-2-carboxylic acid; piperidine-2-carboxylic acid; tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-aza-bicyclo-[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro(bicyclo[2.2.1]-heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6,9}$]-decane-3-carboxylic acid; decahydrocyclohepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid; hydroxyproline-2-carboxylic acid; which can all be optionally substituted (see the following formulae):

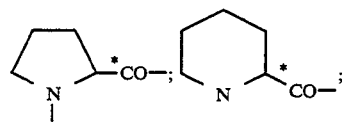

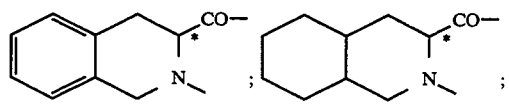

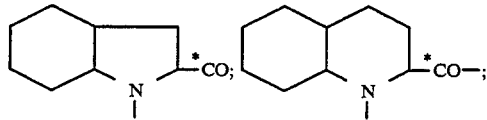

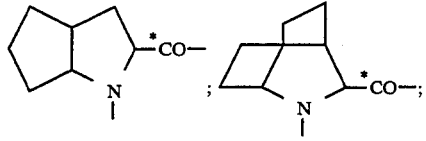

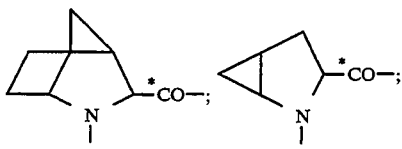

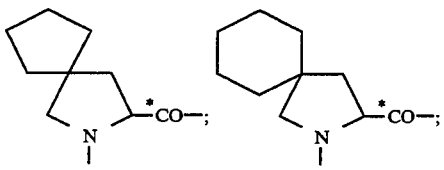

-continued

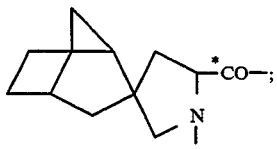

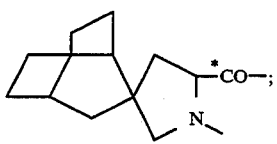

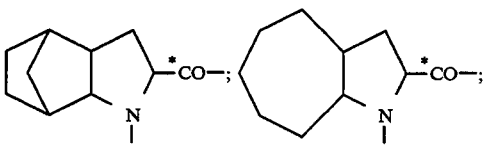

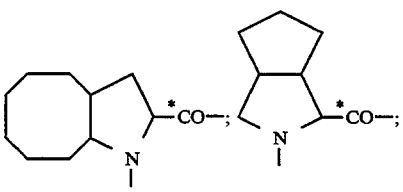

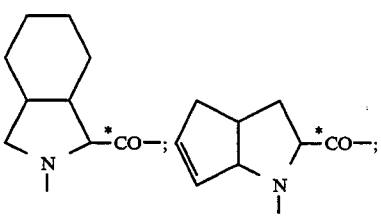

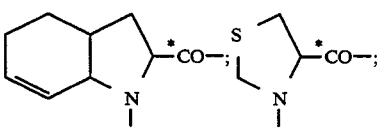

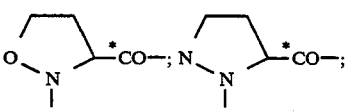

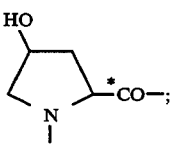

The heterocycles on which the abovementioned radicals are based are known, for example, from U.S. Pat. Nos. 4,344,949; 4,374,847; 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111 873; EP-A 271,865 and EP-A 344,682.

Dipeptides can contain natural or unnatural amino acids, imino acids and also azaamino acids as components. The natural or unnatural amino acids, imino acids, azaamino acids and dipeptides can furthermore also be present as esters or amides, such as, for example, methyl ester, ethyl amide, semicarbazide or ω-amino-$(C_4-C_8)$-amide.

Functional groups of the amino acids, imino acids and dipeptides can be present in protected form. Suitable protective groups such as, for example, urethane protective groups, carboxyl protective groups and side chain protective groups are described in Hubbuch, Kontakte (Merck) 1979, No. 3, pages 14 to 23 and in Büllesbach, Kontakte (Merck) 1980, No. 1, pages 23 to 35. The following may be mentioned in particular: Aloc, Pyoc, Fmoc, Tcboc, Z, Boc, Ddz, Bpoc, Adoc, Msc, Moc, $Z(NO_2)$, $Z(Hal_n)$, Bobz, Iboc, Adpoc, Mboc, Acm, tert-butyl, OBzl, ONbzl, OMbzl, Bzl, Mob, Pic, Trt.

Physiologically tolerable salts of the compounds of the general formula I are in particular pharmaceutically utilisable or non-toxic salts.

Such salts are formed, for example, from compounds of the general formula I which contain acidic groups, for example carboxyl, using alkali metals or alkaline earth metals, such as, for example, Na, K, Mg and Ca, and also with physiologically tolerable organic amines, such as, for example, triethylamine and tris(2-hydroxyethyl)amine.

Compounds of the general formula I which contain basic groups, for example an amino group or a guanidino group, form salts with organic acids, such as, for example, hydrochloric acid, sulphuric acid or phosphoric acid and with organic carboxylic or sulphonic acids, such as, for example, acetic acid, citric acid, benzoic acid, maleic acid, fumaric acid, tartaric acid and p-toluenesulphonic acid.

Preferred compounds of the general formula I are those in which

Y denotes —$(CH_2)_m$—CO—, where m represents 1 or 2, or

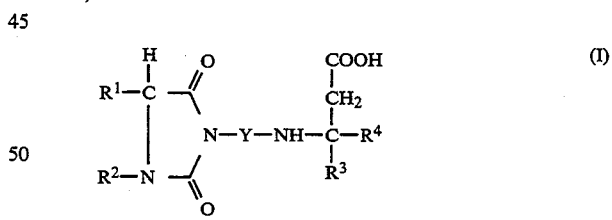

$R^1$ denotes —$CH_2$—$C_6H_4$—NH—C(=NH)—$NH_2$; —$CH_2$-$CH_6H_4$—C(=NH)—$NH_2$ or —$CH_2$—$C_6H_4$—$CH_2$—$NH_2$;

$R^2$ denotes hydrogen or methyl;

$R^3$ denotes hydrogen; and $R^4$ denotes —CO—NH—$R^5$, where —NH—$R^5$ represents an ω-amino-$(C_2-C_8)$-alkyl amide of an α-amino acid residue.

—NH—$R^5$ is particularly preferably represented by the 4-aminobutyl amide of the valine, lysine, phenylalanine or phenylglycine residues.

The compounds of the general formula I according to the invention can be prepared by fragment condensation of a compound of the general formula III

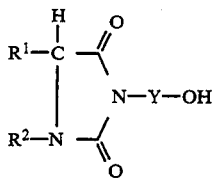 (III)

with a compound of the general formula IV

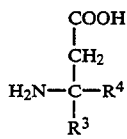 (IV)

where the radicals $R^1$ to $R^4$ and Y are defined as indicated above.

For condensation of the compounds of the general formula III with those of the general formula IV, the methods of peptide chemistry known per se are advantageously used (see, for example, Houben-Weyl, Methoden der organischen Chemie (Methods of organic chemistry) Volume 15/1 and 15/2, Stuttgart, 1974).

To do this, it is necessary as a rule that amino groups contained in $R^1$ and $R^4$ are protected by reversible protective groups. The same applies to the carboxyl groups of the compound of the general formula IV, which is preferably present as a benzyl or tert-butyl ester. Protection of amino groups is unnecessary if the amino groups to be generated are present as nitro or cyano groups and are only formed after coupling by hydrogenation.

After coupling, the protective groups present are removed in a suitable manner. For example, $NO_2$ groups (guanidino protection), benzyloxycarbonyl groups and benzyl esters can be removed by hydrogenation. Protective groups of the tert-butyl type are cleaved by acid, while the 9-fluorenylmethoxycarbonyl radical is removed by secondary amines.

The starting compounds of the general formula III can be obtained as follows:

By reaction of amino acids, N-alkylamino acids or preferably their methyl, ethyl, benzyl or tert-butyl esters, for example a compound of the general formula V

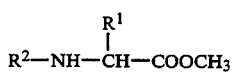 (V)

with an isocyanatoalkanecarboxylic acid ester, for example of the general formula VI $$O=C=N-(CH_2)_m-COOCH_3 \quad (VI)$$

in which $R^1$, $R^2$ and m are defined as indicated above, urea derivatives are obtained, for example of the general formula VII

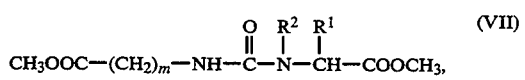 (VII)

which cyclise by heating with acid with hydrolysis of the ester functions to give compounds of the general formula IIIa

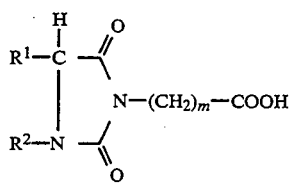 (IIIa)

During the urea synthesis, guanidino groups can be blocked by protective groups, such as $NO_2$ or Mtr. Amino groups in the side chain must likewise be present in protected form (for example as Boc or Z derivatives) or additionally as an $NO_2$ or cyano function which can later be reduced to the amino group or, in the case of the cyano group, also be converted into the formamidino group.

Compounds of the general formula IIIb

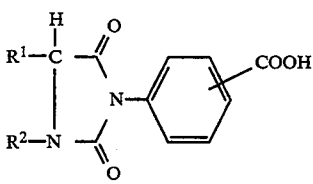 (IIIb)

can be obtained analogously if, instead of isocyanatoalkanecarboxylic acid esters, the isocyanates of the aminobenzoic acid esters are employed.

Compounds of the general formula IIIc

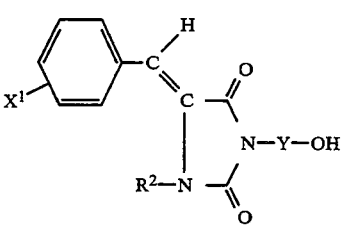 (IIIc)

can be obtained by reaction of hydantoins of the general formula VIII

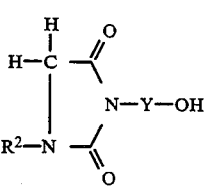 (VIII)

with aldehydes of the general formula IX

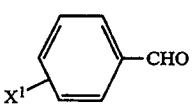 (IX)

analogously to Gränacher and Landolt, Helv. Chim. Acta 10 (1927) 808.

Otherwise, hydantoins of the general formula Xa

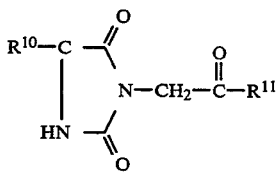

(Xa)

in which $R^{10}$ denotes any desired amino acid side chain and $R^{11}$ denotes an amide, an amino acid residue or a peptide residue, very commonly result by basic treatment of alkoxycarbonyl peptides or aralkoxycarbonyl peptides of the general formula X

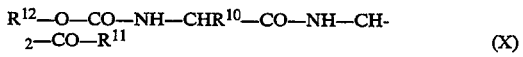

(X)

in which $R^{10}$ and $R^{11}$ are defined as indicated above and $R^{12}$ denotes benzyl or tert-butyl (J. S. Fruton and M. Bergmann, J. Biol. Chem. 145 (1942) 253-265; C. A. Dekker, S. P. Taylor, jr. and J. S. Fruton, J. Biol. Chem. 180 (1949) 155-173; M. E. Cox, H. G. Carg, J. Hollowood, J. M. Hugo, P.M. Scopes and G. T. Young, J. Chem. Soc. (1965) 6806-6813; W. Voelter and A. Altenburg, Liebigs Ann. Chem. (1983) 1641-1655; B. Schwenzer, E. Weber and G. Losse, J. Prakt. Chem. 327 (1985) 479-486). In this case, however, the N-terminal amino acid racemises and the hydantoin hydrolyses to the urea derivative

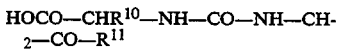

(W. Voelter and A. Altenburg, Liebigs Ann. Chem. (1983) 1641-1655).

In comparison, a mild method is cyclisation to give the hydantoins from compounds of the general formula X by treatment with tetrabutylammonium fluoride in tetrahydrofuran under reflux (J. Pless, J. Org. Chem. 39 (1974) 2644-2646).

A further possibility of a mild cyclisation is trimethylsilylation of the peptide bond between the N-terminal amino acid and the following glycine using bistrimethylsilyltrifluoroacetamide in acetonitrile (4 hours under reflux) (J. S. Davies, R. K. Merritt and R. C. Treadgold, J. Chem. Soc. Perkin Trans. I (1982) 2939-2947).

The guanylation of the amino function can be carried out using the following reagents:

1 O-Methylisothiourea (S. Weiss and H. Krommer, Chemiker Zeitung 98 (1974) 617-618), 2. S-Methylisothiourea (R. F. Borne, M. L. Forrester and I. W. Waters, J. Med. Chem. 20 (1977) 771-776), 3. Nitro-S-methylisothiourea (L. S. Hafner and R. E. Evans, J. Org. Chem. 24 (1959) 1157), 4. Formamidinosulphonic acid (K. Kim, Y.-T. Lin and H. S. Mosher, Tetrah. Lett. 29 (1988) 3183-3186), 5. 3,5-Dimethyl-1-pyrazolylformamidinium nitrate (F. L. Scott, D. G. O'Donovan and J. Reilly, J. Amer. Chem. Soc. 75 (1953) 4053-4054).

Formamidines can be prepared from the corresponding cyano compounds by addition of alcohols (for example methanol or ethanol) in acidic anhydrous medium (for example dioxane, methanol or ethanol) and subsequent treatment with ammonia in alcohols (for example isopropanol, methanol or ethanol) (G. Wagner, P. Richter and Ch. Garbe, Pharmazie 29 (1974) 12-55). A further method of preparing formamidines is the addition of $H_2S$ to the cyano group, followed by a methylation of the resulting thioamide and subsequent reaction with ammonia (GDR Patent No. 235,866).

The starting peptides of the general formula IV are as a rule synthesised stepwise from the C-terminal end. Formation of peptide bonds can be carried out using the known coupling methods of peptide chemistry.

The compounds of the general formula I and their physiologically tolerable salts can be administered as medicines per se on their own, in mixtures with one another or in the form of pharmaceutical preparations which permit enteral or parenteral use and which contain, as active constituent, an effective dose of at least one compound of the general formula I or of a salt thereof, in addition to customary pharmaceutically innocuous excipients and additives. The preparations normally contain about 0.5 to 90% by weight of the therapeutically active compound.

The medicines can be administered orally, for example in the form of pills, tablets, coated tablets, sugar-coated tablets, granules, hard and soft gelatine capsules, solutions, syrups, emulsions, suspensions or aerosol mixtures. Administration can also be carried out, however, rectally, for example in the form of suppositories, or parenterally, for example in the form of injection solutions or microcapsules, percutaneously, for example in the form of ointments or tinctures or nasally, for example in the form of nasal sprays.

The pharmaceutical preparations can be prepared in a manner known per se, pharmaceutically inert inorganic or organic excipients being used. For the preparation of pills, tablets, coated tablets and hard gelatine capsules, lactose, maize starch or derivatives thereof, talc, stearic acid or its salts, etc., for example, can be used. Excipients for soft gelatine capsules and suppositories are, for example, fats, waxes, semi-solid and liquid polyols, natural or hardened oils, etc. Suitable excipients for the preparation of solutions and syrups are, for example, water, sucrose, dextrose, glucose, polyols etc. Suitable excipients for the preparation of injection solutions are water, alcohols, glycerol, polyols or vegetable oils, etc. Suitable excipients for microcapsules or implants are, for example, copolymers of glycolic acid and lactic acid.

Apart from the active compounds and excipients, the pharmaceutical preparations can additionally contain additives such as, for example, fillers, extenders, disintegrants, binders, lubricants, wetting agents, stabilisers, emulsifiers, preservatives, sweeteners, colorants, flavourings or aromatisers, thickeners, diluents, buffer substances, and also solvents or solubilisers or agents for achieving a depot effect as well as salts for changing the osmotic pressure, coating agents or antioxidants. They can also contain two or more compounds of the general formula I or their physiologically tolerable salts and additionally one or more other therapeutically active substances.

Other therapeutically active substances of this type are, for example, agents promoting the circulation, such as dihydroergocristine, nicergoline, buphenine, nicotinic acid and its esters, pyridylcarbinol, bencyclan, cinnarizine, naftidrofuryl, raubasine and vincamine; positively inotropic compounds, such as digoxin, acetyldigoxin, metildigoxin and lanthanoglycosides; coronary dilators, such as carbochromen; dipyramidol, nifedipine and perhexiline; antianginal compounds, such as isosorbide dinitrate, isosorbide mononitrate, glycerol nitrate, molsidomine and verapamil; β-blockers, such as propranolol, oxprenolol, atenolol, metoprolol and penbutolol. The compounds may moreover be combined with other nootropic substances, such as, for example, piracetam, or CNS-active substances, such as pirlindol, sulpiride, etc.

The dose can vary within wide limits and is to be adapted to the individual conditions in each individual case. In general, in the case of oral administration a daily dose of about 0.1 to 1 mg/kg, preferably 0.3 to 0.5 mg/kg, of body weight is appropriate to achieve effective results, in the case of intravenous administration the daily dose is in general about 0.01 to 0.3 mg/kg, preferably 0.05 to 0.1 mg/kg, of body weight. The daily dose is normally divided, in particular in the case of the administration of relatively large amounts, into several, for example 2, 3 or 4, part administrations. In some cases, depending on individual behaviour, it may be necessary to deviate upwards or downwards from the given daily dose. Pharmaceutical preparations normally contain 0.2 to 50 mg, preferably 0.5 to 10 mg, of active compound of the general formula I or one of its physiologically tolerable salts per dose.

The compounds of the formula I according to the invention have the ability to inhibit cell-cell adhesion which is due to the interaction of Arg-Gly-Asp-containing proteins, such as fibronectin, fibrinogen or the yon Willebrand factor, with the so-called integrins. Integrins are transmembrane glycoproteins, receptors for Arg-Gly-Asp-containing cell matrix glycoproteins (E. Ruoslahti and M. D. Pierschbacher, Science 238 (1987) 491–497; D. R. Phillips, I. F. Charo, L. V. Parise and L. A. Fitzgerald, Blood 71 (1988) 831–843). They additionally inhibit the binding of other adhesive proteins, such as vitronectin, collagen and laminin, to the corresponding receptors on the surface of various types of cell.

The compounds of the general formula I according to the invention inhibit platelet aggregation, the metastasis of carcinoma cells and osteoclast binding to the bone surfaces.

The hydantoin derivatives of the general formula I are used acutely in risk of thrombosis and chronically in the prevention of arteriosclerosis and thrombosis, for example in the therapy and prophylaxis of arterial vascular diseases, such as in acute myocardial infarct, secondary prevention of myocardial infarct, reocclusion prophylaxis after lysis and dilatation (PCTA), unstable angina pectoris, transitory ischaemic attacks, strokes, coronary bypass operation including bypass reocclusion prophylaxis, pulmonary embolism, peripheral arterial occlusive disease, dissecting aneurysm; in the therapy of venous and microcirculatory vascular disorders, such as deep vein thrombosis, disseminated intravascular clotting, post-operative and post-partum trauma, surgical or infectious shock, septicaemia or in hyperactive platelet diseases, thrombotic thrombocytopenic purpura, preeclampsia, premenstrual syndrome, dialysis or extracorporeal circulation; a further use is during cancer operations and also prophylactically in cancer. Osteoporosis can also be prevented by inhibition of osteoclast binding to the bone surface.

The compounds are tested in particular for their inhibitory action in blood platelet aggregation and the adhesion of fibrinogen to blood platelets. Gel-filtered blood platelets from human donor blood are used, which are activated with ADP or thrombin.

EXAMPLES

The products were identified by means of mass spectra and/or NMR spectra.

EXAMPLE 1

(5-(S)-(3-Guanidinopropyl)-2,4-dioxoimidazolidin-3-yl)acetyl-L-aspartyl-L-phenylalanine (4-aminobutyl) amide acetate 1a: Z-Phe-NH-$(CH_2)_4$—NH-Boc 5.98 g ( 20 mmol ) of N-benzyloxycarbonyl-L-phenylalanine and 4.49 g (20 mmol) of 4-(tert-butoxycarbonylamino)butylamine hydrochloride are dissolved in 100 ml of dimethylformamide and cooled to 0° C. in an ice-bath. After addition of 2.7 g (20 mmol) of hydroxybenzotriazole, 4.4 g (20 mmol) of DCCI and 2.54 ml (20 mmol) of N-ethylmorpholine, the reaction is stirred overnight. The precipitated urea is filtered off with suction and the solution is evaporated in a high vacuum. The residue is taken up in 200 ml of ethyl acetate and the organic phase is extracted with water, sodium hydrogen carbonate solution and potassium hydrogen sulphate solution and dried over magnesium sulphate. After filtration and concentration, 8.2 g (87%) of amorphous product are obtained.

1b: H-Phe-NH-$(CH_2)_4$—NH—Boc hydrochloride 8.2 g (17.5 mmol) of Z-Phe-NH-$(CH_2)_4$—NH—Boc are dissolved in 300 ml of methanol and treated with 1.5 g of Pd/C. Hydrogen is then introduced and the pH is maintained at 4 by addition of methanolic hydrochloric acid. After completion of the reaction, the mixture is filtered and the filtrate is evaporated. After triturating with ether, 6.5 g (100%) of amorphous product are obtained.

1c: H-L-Aspartyl(OtBu)-L-phenylalanine-NH-$(CH_2)_4$NH—Boc hydrochloride 5.6 g (17.4 mmol) of Z-Asp(OtBu)-OH and 6.5 g (17.5 mmol) of H-Phe-NH-$(CH_2)_4$—NH-Boc hydrochloride are dissolved in 100 ml of dimethylformamide. After addition of 2.3 g (17 mmol) of hydroxybenzotriazole, 4.4 g (21.3 mmol) of DCCI and 2.2 ml (17.3 mmol) of N-ethylmorpholine, the reaction is stirred overnight. After completion of the reaction, the mixture is concentrated in vacuo. The residue is taken up in ethyl acetate and the organic phase is extracted with water and sodium hydrogen carbonate solution and then dried using magnesium sulphate. After filtration and concentration, 9.7 g of crude product are obtained, which is purified by chromatography.

The combined fractions are hydrogenated as described in 1b. The residue from the hydrogenation is dissolved in 50 ml of ethyl acetate and precipitated using petroleum ether. 4.9 g are obtained.

FAB-MS 507.3 $(M+H)^+$

1d: 5-(S)-(3-Guanidinopropyl)-2,4-dioxoimidazolidin-3-yl)acetyl-L-aspartyl(OtBu)-L-phenylalanine (4-Boc-aminobutyl) amide 977 mg (1.8 mmol) of H-L-aspartyl(OtBu)-L-phenylalanine-NH-$(CH_2)_4$—NH-Boc hydrochloride and 500 mg of 5-(S)-(3-guanidinopropyl)-2,4-dioxoimidazolidin-3-yl)acetic acid are dissolved in 5 ml of dimethylformamide. 243 mg (1.8 mmol) of hydroxybenzotriazole and 412 mg (2 mmol) of DCCI are added to the solution and it is stirred overnight. After completion of the reaction, the solution is concentrated and the residue is chromatographed on silica gel without further treatment (eluent: $CH_2Cl_2$, $CH_3OH$, acetic acid, water=85:10:2.5:2.5). 1.03 g (76%) of product are isolated.

FAB-MS 746.6 (M+H)+

1e: (5-(S)-(3-Guanidinopropyl)-2,4-dioxoimidazolidin-3-yl)acetyl-L-aspartyl-L-phenylalanine (4-aminobutyl) amide acetate 1 g (1.38 mmol) of 5-(S)-(3-guanidinopropyl)-2,4-dioxoimidazolidin-3-yl)acetyl-L-aspartyl(OtBu)-L-phenylalanine 4-Boc-aminobutyl amide are stirred at room temperature for 1 hour in 15 ml of 90% strength aqueous trifluoroacetic acid. The solution is then concentrated, the residue is taken up in water and the solution is treated with ion exchanger IRA-93 until a pH of 4 is obtained. The solution is freeze-dried and the residue (880 mg) is chromatographed on Sephadex LH20 using 1M acetic acid. After concentration and freeze-drying, 735 mg (90%) of product are obtained.

FAB-MS 590.1 (M+H)+

EXAMPLE 2

(5-(S)-(3-Guanidinopropyl)-2,4-dioxoimidazolidin-3-yl)acetyl-L-aspartyl-L-phenylalanine (6-aminohexyl) amide acetate This compound was prepared analogously to the method described in Example 1.

FAB-MS 618.1 (M+H)+

EXAMPLE 3

(5-(S)-(3-Guanidinopropyl)-2,4-dioxoimidazolidin-3-yl)acetyl-L-aspartyl-L-phenylalanine (8-aminooctyl) amide acetate This compound was prepared analogously to the method describd in Example 1.

FAB-MS 646 (M+H)+

EXAMPLE 4

(5-(R,S)-(4-Formamidinobenzyl)-2,4-dioxoimidazolidin-3-yl)acetyl-L-aspartyl-L-phenylalanine (4-aminobutyl) amide acetate This compound was prepared analogously to the method described in Example 1.

FAB-MS 623 (M+H)+

EXAMPLE 5

(5-(R,S)-(4-Formamidinobenzyl)-2,4-dioxoimidazolidin-3-yl)acetyl-L-aspartyl-L-phenylalanine (6-aminohexyl) amide acetate This compound was prepared analogously to the method described in Example 1.

FAB-MS 651 (M+H)+

EXAMPLE 6

(5-(R,S)-(4-Formamidinobenzyl)-2,4-dioxoimidazolidin-3-yl)acetyl-L-aspartyl-L-phenylalanine (8-aminooctyl) amide acetate This compound was prepared analogously to the method described in Example 1.

FAB-MS 679 (M+H)+

EXAMPLE 7

(5-(R,S)-(4-Formamidino-benzyl)-2,4-dioxoimidazolidin-3-yl)acetyl-L-aspartyl-L-lysine (4-aminobutyl) amide 7a: H-Aspartyl(OtBu)-L-lysine(Boc)-NH-(CH$_2$)$_4$—NH—Boc hydrochloride 1.17 ml of N-ethylmorpholine and 1.98 g of DCCI are added at 0° C. to a solution of 5.3 g of H-Lys(Boc)-NH-(CH$_2$)$_4$—NH—Boc tosylate, 2.91 g of Z-Asp(OtBu)-OH and 1.21 g of hydroxybenzotriazole in 20 ml of dimethylformamide. The mixture is stirred at 0° C. for 1 hour and at room temperature for 4 hours and allowed to stand overnight at room temperature. The precipitate is filtered off with suction and the filtrate is concentrated in vacuo. The residue is partitioned between ethyl acetate and water. The organic phase is extracted with sodium hydrogen carbonate solution, potassium hydrogen sulphate solution and water and dried over sodium sulphate and concentrated. The residue is triturated with ether and filtered off with suction. The product obtained (5.2 g) is dissolved in 150 ml of methanol and catalytically hydrogenated over Pd/carbon at pH 4.5 using methanolic hydrochloric acid in an autoburette. After reaction was complete, the catalyst was filtered off with suction and the filtrate was concentrated.

Yield: 4.12 g of amorphous substance $a)_D^{24}=+3.9°$ (c=1, methanol)

7b: (5-(R,S)-(4-Formamidinobenzyl)-2,4-dioxoimidazolidin-3-yl)acetyl-L-aspartyl(OtBu)-L-lysine(-Boc) (4-Boc-aminobutyl) amide 1.1 g of DCCI are added at 0° C. to a suspension of 1.54 g of (5-(R,S)-(4-formamidinobenzyl)-2,4-dioxoimidazolidin-3-yl) acetic acid, 3.1 g of H-aspartyl(OtBu)-L-lysine(Boc)-NH-(CH$_2$)$_4$-NH-BOC hydrochloride and 675 mg of hydroxybenzotriazole in 20 ml of dimethylformamide. The mixture is stirred at 0° C. for 1 hour and at room temperature for 4 hours and allowed to stand overnight at room temperature. The precipitate is filtered off with suction and the filtrate is concentrated in vacuo. For purification, the substance is chromatographed on silica gel in methylene chloride/methanol/water/acetic acid=8.5:1.5:0.2:0.2.

Yield: 3.26 g of amorphous substance $a)_D^{24}=-28.7°$ (c=1, methanol)

7c: (5-(R,S)-(4-Formamidinobenzyl)-2,4-dioxoimidazolidin-3-yl)acetyl-L-aspartyl-L-lysine (4-aminobutyl) amide diacetate 3.15 g of (5-(R,S)-(4-formamidinobenzyl)-2,4-dioxoimidazolidin-3-yl)acetyl-L-aspartyl(OtBu)-L-lysine(-Boc) (4-Boc-aminobutyl) amide are dissolved in 30 ml of 90% strength aqueous trifluoroacetic acid. After one hour at room temperature, the mixture is concentrated in vacuo and the residue is partitioned between water and diethyl ether. The aqueous phase (30 ml) is chromatographed on 50 ml of Amberlite IR 93 (acetate form) and water as the eluent. The eluate is lyophilised and gives 2.42 g of substance. For purification, the substance is chromatographed on Sephadex LH20 (200×4 cm) in a mixture of acetic acid, n-butanol and water. The fractions containing pure substance are concentrated, dissolved in water and freeze-dried Yield 2.27 g $a)_D^{24}=-35.2°$ (c=1, water)

EXAMPLE 8

(5-(R,S)-(3-Guanidinopropyl)-2,4-dioxoimidazolidin-3-yl)acetyl-L-aspartyl-L-valine (4-aminobutyl) amide This compound was prepared analogously to the method described in Example 1.

FAB-MS 541 (M+H) +

EXAMPLE 9

(5-(R,S)-(4-Formamidinobenzyl)-2,4-dioxoimidazolidin-3-yl)acetyl-L-aspartyl-L-phenylglycine (4-aminobutyl) amide This compound was prepared analogously to the method described in Example 1.

FAB-MS 608 (M+H)+

Example A

Emulsions containing 3 mg of active compound per 5 ml can be prepared according to the following recipe:

| | | |
|---|---|---|
| Active compound | 0.06 g | |
| Neutral oil | q.s. | |
| sodium carboxymethylcellulose | 0.6 g | |
| Polyoxyethylene stearate | q.s. | |
| Pure glycerol | 0.6 to 2 g | |
| Aromatics | q.s. | |
| Water (demineralised or distilled) | to 100 ml | |

Example B

Tablets can be prepared according to the following formulation:

| | |
|---|---|
| Active compound | 2 mg |
| Lactose | 60 mg |
| Maize starch | 30 mg |
| Soluble starch | 4 mg |
| Magnesium stearate | 4 mg |
| | 100 mg |

Example C

The following composition is suitable for the preparation of soft gelatine capsules containing 5 mg of active compound per capsule:

| | |
|---|---|
| Active compound | 5 mg |
| Mixture of triglycerides from coconut oil | 150 mg |
| Capsule contents | 155 mg |

Example D

The following formulation is suitable for the preparation of sugar-coated tablets:

| | |
|---|---|
| Active compound | 3 mg |
| Maize starch | 100 mg |
| Lactose | 55 mg |
| Sec. calcium phosphate | 30 mg |
| Soluble starch | 3 mg |
| Magnesium stearate | 5 mg |
| Colloidal silica | 4 mg |
| | 200 mg |

Example E

Sugar-coated tablets containing an active compound according to the invention and another therapeutically active substance:

| | |
|---|---|
| Active compound | 6 mg |
| Propanolol | 40 mg |
| Lactose | 90 mg |
| Maize starch | 90 mg |
| Sec. calcium phosphate | 34 mg |
| Soluble starch | 3 mg |
| Magnesium stearate | 3 mg |
| Colloidal silica | 4 mg |
| | 270 mg |

Example F

Sugar-coated tablets containing an active compound according to the invention and another therapeutically active substance:

| | |
|---|---|
| Active compound | 5 mg |
| Pirlindol | 5 mg |
| Lactose | 60 mg |
| Maize starch | 90 mg |
| Sec. calcium phosphate | 30 mg |
| Soluble starch | 3 mg |
| Magnesium stearate | 3 mg |
| Colloidal silica | 4 mg |
| | 200 mg |

Example G

Capsules containing an active compound according to the invention and another therapeutically active substance:

| | |
|---|---|
| Active compound | 5 mg |
| Nicergoline | 5 mg |
| Maize starch | 185 mg |
| | 195 mg |

Example H

Injection solutions containing 1 mg of active compound per ml can be prepared according to the following recipe:

| | |
|---|---|
| Active compound | 1.0 mg |
| Polyethylene glycol 400 | 0.3 mg |
| Sodium chloride | 2.7 mg |
| Water for injection purposes to | 1 ml |

Pharmacological Data

The inhibition of the binding of fibrinogen to its receptor (glycoprotein IIb/IIIa) by the compounds according to the invention is tested on intact, gel-filtered human platelets. The $K_i$ value of the inhibition of binding of $^{125}$I-fibrinogen after stimulation with ADP (10 µM) is given.

References

J. S. Bennett and G. Vilaire, J. Clin. Invest. 64 (1979), 1393–1401

E. Kornecki et al., J. Biol. Chem. 256 (1981), 5695–5701

G. A. Marguerie et al., J. Biol. Chem. 254 (1979), 5357–5363

G. A. Marguerie et al., J. Biol. Chem. 255 (1980), 154–161

| Example | $K_i$ (µM), ADP-stimulated |
|---|---|
| 1 | 2.50 |
| 2 | 2.44 |
| 3 | 3.21 |
| 4 | 0.32 |
| 7 | 0.17 |

As a functional test, the inhibition of aggregation of gel-filtered human platelets by the compounds according to the invention is measured after ADP or thrombin stimulation. The $IC_{50}$ value of the inhibition is given.

Reference

G. A. Marguerie et al., J. Biol. Chem. 254 (1979), 5357-5363

| Example | ADP-stimulated | $IC_{50}$ (μM), Thrombin-stimulated |
|---------|----------------|-------------------------------------|
| 1 | 1.5 | 2.0 |
| 2 | 3.0 | 3.5 |
| 3 | 5.0 | 3.0 |
| 4 | 0.45 | 1.0 |
| 7 | 0.25 | 0.6 |

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

It is claimed:

1. Compound of the formula I

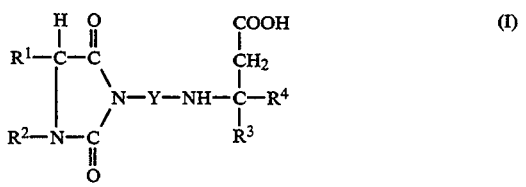

in which Y denotes —$(CH_2)_m$—CO—, where m represents an integer from 1 to 4, or

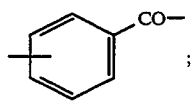

$R^1$ denotes —$(CH_2)_n$—NH—X, where n represents an integer from 1 to 6, —$(CH_2)_p$—$C_6H_4$—NH—X, —$(CH_2)_p$—$C_6H_4$—C(=NH)—$NH_2$ or —$(CH_2)_p$—$C_6$-$H_4$—$CH_2$—NH—X, where p in each case represents 1 or 2, or where

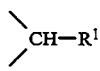

is replaced by

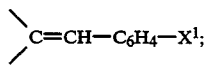

$X^1$ denotes —NHX, —$CH_2NHX$ or —C(=NH)—$NH_2$;

X denotes hydrogen, ($C_1$-$C_6$)-alkyl or a radical of the formula II

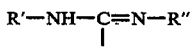

where R' and R'' independently of one another represent hydrogen or ($C_1$-$C_6$)-alkyl;

$R^2$ denotes hydrogen or ($C_1$-$C_6$)-alkyl;

$R^3$ denotes hydrogen or phenyl;

$R^4$ denotes —$COOR^5$, —CO—N($CH_3$)—$R^5$ or —CO—NH—$R^5$;

$R^5$ denotes ($C_1$-$C_8$)-alkyl which is substituted a) by amino-($C_2$-$C_{14}$)-alkylaminocarbonyl, where the alkyl radical is unsubstituted or is substituted by hydroxyl, amino, mercapto, ($C_{1-C8}$)-alkoxy, phenyl or phenyl-($C_1$-$C_4$)-alkyl, and which b) is additionally substituted by from zero to two identical or different radicals selected from the group consisting of hydroxyl, hydroxycarbonyl, aminocarbonyl, amino, mercapto, ($C_1$-$C_8$)-alkoxy, ($C_1$-$C_8$)-alkoxycarbonyl, phenyl-($C_1$-$C_3$)-alkoxycarbonyl, ($C_3$-$C_8$)-cycloalkyl and a radical $R^6$;

$R^6$ denotes phenyl, phenyl-($C_1$-$C_4$)-alkyl or denotes a radical $R^7$, where the phenyl radical is unsubstituted or is substituted by one or more identical or different radicals selected from the group consisting of ($C_1$-$C_8$)-alkyl, ($C_1$-$C_8$)-alkoxy, halogen, nitro and trifluoro-methyl;

$R^7$ denotes —$NR^8R^9$, —$OR^8$, —$SR^8$, an amino acid side chain, a natural or unnatural amino acid radical, imino acid radical or dipeptide radical or an ester or amide thereof, or denotes a radical —$COR^{7'}$, in which $R^{7'}$ is defined as $R^7$;

$R^8$ denotes hydrogen, ($C_2$-$C_8$)-alkyl, phenyl-($C_1$-$C_4$)-alkyl, ($C_1$-$C_8$)-alkylcarbonyl, ($C_1$-$C_8$)-alkoxycarbonyl, phenylcarbonyl, phenyl-($C_1$-$C_4$)-alkylcarbonyl, or phenyl-($C_1$-$C_4$)-alkoxycarbonyl;

$R^9$ denotes hydrogen, ($C_1$-$C_8$)-alkyl, phenyl or phenyl-($C_1$-$C_4$)-alkyl;

or their physiologically tolerable salts.

2. Compound according to claim 1, in which

Y denotes —$(CH_2)_m$—CO—, where m represents 1 or 2, or

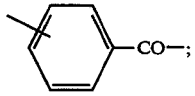

$R^1$ denotes —$CH_2$-$C_6H_4$—NH—C(=NH)—$NH_2$; —$CH_2$-$C_6H_4$—C(=NH) —$NH_2$ or —$CH_2$-$C_6$-$H_4$—$CH_2$—$NH_2$;

$R^2$ denotes hydrogen or methyl;

$R^3$ denotes hydrogen; and $R^4$ denotes —CO—NH—$R^5$, where —NH—$R^5$ represents the radical of an Ω-amino-($C_2$-$C_8$)-alkyl amide of an α-amino acid.

3. Compounds according to claim 2, in which —NH—$R^5$ is the radical of the 4-aminobutyl amide of valine, lysine, phenylalanine or phenylglycine.

4. Process for inhibiting platelet aggregation, metastasis of carcinoma cells or osteoclast formation on the bone surface comprising administering to a patient in need thereof an effective dose of a compound according to claim 1.

5. Pharmaceutical preparation, characterised in that it contains one or more compounds of the general formula I of claim 1 or a physiologically tolerable salt thereof as active compound together with pharmaceutically acceptable excipients and additives and, optionally one or more other pharmacological active compounds.

* * * * *